United States Patent [19]

Sakurai et al.

[11] Patent Number: 5,060,619
[45] Date of Patent: Oct. 29, 1991

[54] ELECTROSTATIC CAPACITY TYPE FUEL CONCENTRATION MONITORING UNIT WITH TEMPERATURE DEPENDENT FLUCTUATION COMPENSATING FEATURE

[75] Inventors: Osamu Sakurai; Kazumitsu Kobayashi; Hideki Kano, all of Isezaki; Kiyoshi Takeuchi, Tokyo, all of Japan

[73] Assignees: Japan Electronic Control Systems Co., Ltd., Isezaki; Nissan Motor Company, Limited, Yokohama, both of Japan

[21] Appl. No.: 611,276

[22] Filed: Nov. 9, 1990

[30] Foreign Application Priority Data

Nov. 10, 1989 [JP] Japan .................................. 1-293676
May 30, 1990 [JP] Japan .................................. 2-140326

[51] Int. Cl.$^5$ ........................ F02D 41/04; F02B 75/12; G01F 1/56
[52] U.S. Cl. .................................. 123/494; 123/1 A; 123/381; 73/61.1 R; 73/117.3
[58] Field of Search ............... 123/1 A, 381, 488, 494, 123/575; 73/61.1 R, 117.3, 861.08, 304 C; 324/453

[56] References Cited

U.S. PATENT DOCUMENTS

| | | | |
|---|---|---|---|
| 4,438,749 | 3/1984 | Schwippert | 123/381 X |
| 4,706,629 | 11/1987 | Wineland et al. | 123/494 X |
| 4,770,129 | 9/1988 | Miyata et al. | 123/494 X |
| 4,905,655 | 3/1990 | Maekawa | 123/494 |
| 4,945,863 | 8/1990 | Schmitz et al. | 123/494 X |
| 4,955,345 | 9/1990 | Brown et al. | 123/381 |
| 4,967,714 | 11/1990 | Inoue | 123/1 A |
| 4,971,015 | 11/1990 | Gonze | 123/494 |
| 4,974,552 | 12/1990 | Sickafus | 123/494 X |
| 4,993,391 | 2/1991 | Kuribara et al. | 123/1 A X |
| 4,998,518 | 3/1991 | Mitzumoto | 123/1 A X |

Primary Examiner—Willis R. Wolfe
Attorney, Agent, or Firm—Foley & Lardner

[57] ABSTRACT

A fuel concentration monitoring unit includes a fuel temperature dependent error correction circuit in the unit. A fuel concentration indicative voltage signal variation rate set with taking a specific fuel concentration as reference point. The output incorporated in the unit.

10 Claims, 6 Drawing Sheets

ELECTROSTATIC CAPACITY TYPE FUEL CONCENTRATION MONITORING UNIT WITH TEMPERATURE DEPENDENT FLUCTUATION COMPENSATING FEATURE

BACKGROUND OF THE INVENTION

1. Field of the Invention

The present invention relates generally to a fuel concentration monitoring unit for monitoring concentration of particular fuel in a mixture fuel in which different types of fuels are mixed. More particularly, the invention relates to a electrostatic capacity type fuel concentration sensor which is suitable for monitoring concentration of alcohol in a methanol mixed fuel for an automotive internal combustion engine.

2. Description of the Background Art

In the recent days, it is becoming important task to achieve high anti-polution performance in an automotive internal combustion engine. Particularly, reduction of $CO_2$ gas, $NO_x$ gas from exhaust gas is considered important for future automotive technologies. In this aspect, it has been known that alcohol fuel, such as methanol, is better fuel for smaller emission amount of $CO_2$ and $NO_x$. Therefore, in the modern automotive technologies, there have been various attempt to develop automotive engines which can be driven by a mixture fuel of gasoline and alcohol. In such type of internal combustion engine, adjustment of air/fuel ratio and spark ignition timing depending upon alcohol concentration in the mixture fuel is important task in order to optimize engine performance.

Namely, in case of pure gasoline, stoichiometric air/fuel ratio is approximately 14.7:1. In contrast to this, in case of methanol, stoichiometric air/fuel ratio becomes approximately 6.5:1. Therefore, stoichiometric air/fuel ratio varies in substantially wide range depending upon alcohol concentration in the mixture fuel. In fuel injection control for the automotive internal combustion engine, it thus becomes necessary to correct fuel injection amount depending upon alcohol concentration in the mixture fuel. In order to precisely determine an alcohol concentration dependent correction value, it becomes essential to precisely monitor alcohol concentration in the mixture fuel.

In order to monitor alcohol concentration, various types of alcohol concentration monitoring devices have been developed. Typically, the alcohol concentration monitoring devices monitors alcohol concentration by monitoring electric resistance utilizing difference of electric conductivity, by monitoring electrostatic capacity utilizing difference of dielectric constant, or by monitoring reflactive index utilizing difference if reflactive index between the gasoline and alcohol.

In case of the electrostatic capacity type alcohol concentration monitoring device, the alcohol concentration is represented by an electrostatic capacity $C_s$ between a pair of electrodes. Namely, the electrostatic capacity $C_s$ can be expressed by:

$$C_s = \epsilon S / d$$

wherein
 $\epsilon$: dielectric constant
 S: area of electrode
 d: distance between electrodes As is well known, since the dielectric constant of the mixture fuel increases according to increasing of alcohol concentration in the mixture fuel. Therefore, the electrostatic capacity monitored between the electrodes of the alcohol concentration monitoring device may be considered to represent the concentration of alcohol in the mixture fuel. However, the dielectric constant is also variable depending upon temperature of the mixture fuel. Therefore, in order to precisely monitor the alcohol concentration, it becomes necessary to compensate variation of dielectric constant depending upon the fuel temperature. In the prior proposed systems, fuel temperature sensor comprising a thermister, posistor and so forth, are employed to provide fuel temperature indicative data for obtaining the fuel temperature dependent correction value. Such fuel temperature sensors are disposed in fuel piping to monitor the fuel temperature supplied to fuel injection valves. The fuel temperature sensor is connected to a control unit which performs fuel injection control, to supply the fuel temperature indicative data. The control unit is responsive to this fuel temperature indicative data to derive a fuel temperature dependent correction value for correcting the alcohol concentration indicative data supplied from the alcohol concentration monitoring device. Practically, the fuel temperature dependent correction values are set in a form of map or table in a memory unit of the control unit so that the correction value can be derived by map or table look-up in terms of the fuel temperature indicative data.

As can be appreciated, the correction values to be set in the control unit is variable depending upon the type and specification of the alcohol concentration monitoring devices. This implies that the correction values are to be set with respect to specific alcohol concentration monitoring device. Therefore, when different type or specification of alcohol concentration monitoring device is utilized, all correction values have to be updated adapting to the monitoring device to be used.

Furthermore, in the prior proposed systems, the fuel temperature dependent correction for the alcohol concentration indicative data can be done only when the alcohol concentration monitoring device is combined with the control unit. Therefore, in order to perform inspection, it becomes necessary to combine the alcohol concentration monitoring device with the control unit. Otherwise, during inspection, the temperature of the sample fuel has to be adjusted to be lower than a standard temperature for avoiding fuel temperature dependent error. This clearly requires substantial attention for inspection in the production line.

In addition, since the prior proposed system is required to connect the alcohol concentration monitoring device and the fuel temperature sensor to the control unit, separately from each other. Therefore, extra number of wiring harness becomes necessary to increase the cost and possibility of breakage.

SUMMARY OF THE INVENTION

Therefore, it is an object of the present invention to provide a fuel concentration monitoring unit which can solve the defects or drawbacks in the prior art.

Another and more specific object of the invention is to provide a fuel concentration monitoring unit which can output an output signal representative of a concentration of a specific fuel corrected depending upon fuel temperature, and thus does not require fuel temperature dependent correction in a control unit.

A further object of the invention is to provide a fuel concentration monitoring unit which can reduce number of harness for providing precise data of specific fuel concentration.

In order to accomplish aforementioned and other objects, a fuel concentration monitoring unit, according to the present invention, includes a fuel temperature dependent error correction circuit in the unit. A fuel concentration indicative voltage signal variation rate set with taking a specific fuel concentration as reference point. The output incorporated in the unit.

According to one aspect of the invention, an electrostatic capacity type fuel concentration monitoring unit comprises:

a first sensor disposed within a mixture fuel containing a specific type of fuel in a variable mixture rate, said first sensor producing a first sensor signal indicative of concentration of said specific type of fuel;

a second sensor disposed within said mixture fuel for monitoring temperature thereof, said second sensor generating a second sensor signal indicative of temperature of said mixture fuel;

a circuit incorporated in said unit for generating a fuel concentration indicative signal which varies in a given rate across a predetermined reference value set at a predetermined fuel concentration, said circuit being responsive to said second sensor signal to correct said fuel concentration indicative signal value by varying said given rate depending upon said second sensor signal value.

The circuit may include a frequency generator for generating a frequency signal variable of frequency depending upon fuel concentration of said specific type fuel in said mixture fuel, a frequency-to-voltage converter responsive to said frequency signal to produce a voltage signal as said fuel concentration indicative signal. The reference value may be set at a fuel concentration, at which said fuel concentration indicative signal value contain minimum error depending upon fuel temperature represented by said second sensor signal. In such case, the circuit may further include an operational amplifier which receives said fuel concentration indicative signal at a first input terminal and a reference signal representative of said reference value at a second input terminal, and said second sensor is connected in a feedback circuit connecting an output terminal of said operational amplifier and said second input terminal.

In practice, the electrostatic capacity type fuel concentration monitoring unit may monitor an alcohol concentration in said mixture fuel which contains gasoline and alcohol in a variable rate.

According to another aspect of the invention, a fuel injection control system for an automotive internal combustion engine which is designed to be driven by a mixture fuel of at least two mutually different type of fuels, comprises:

a fuel injection valve disposed for injecting fuel into an induction system of said engine for forming an air/fuel mixture to be combustioned within a combustion chamber:

an engine operation monitoring means for monitoring preselected engine operating parameters to produce engine control parameter signal representative of an engine driving condition:

a fuel concentration monitoring unit for monitoring concentration of specific one of said fuels in said mixture fuel, said fuel concentration monitoring unit including a first sensor disposed within a mixture fuel containing a specific type of fuel in a variable mixture rate, said first sensor producing a first sensor signal indicative of concentration of said specific type of fuel;

a second sensor disposed within said mixture fuel for monitoring temperature thereof, said second sensor generating a second sensor signal indicative of temperature of said mixture fuel;

a circuit incorporated in said unit for generating a fuel concentration indicative signal which varies in a given rate across a predetermined reference value set at a predetermined fuel concentration, said circuit being responsive to said second sensor signal to correct said fuel concentration indicative signal value by varying said given rate depending upon said second sensor signal value; and a control unit receiving said engine control parameter signal for deriving a fuel injection amount on the basis thereof and correcting the fuel injection amount with a correction factor derived on the basis of the corrected fuel concentration indicative signal.

BRIEF DESCRIPTION OF THE DRAWINGS

The present invention will be understood more fully from the detailed description given herebelow and from the accompanying drawings of the preferred embodiments, which, however, should not be taken to limit the invention to the specific embodiments but are for explanation and understanding only.

In the drawings.

DESCRIPTION OF THE PREFERRED EMBODIMENT

Figure 1:
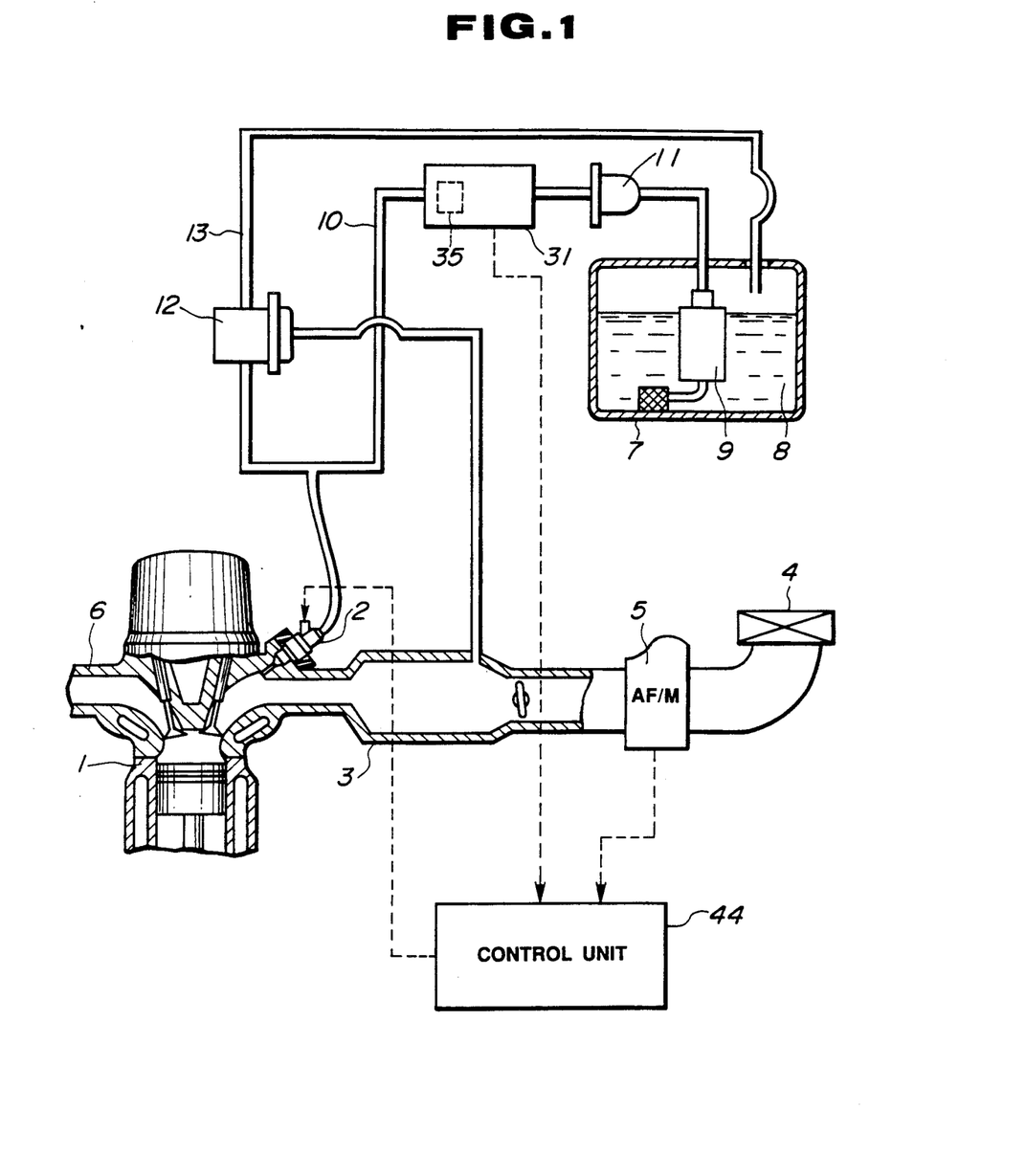
FIG. 1 is a block diagram showing a fuel injection system for an automotive internal combustion engine, to which the preferred embodiment of a fuel concentration monitoring unit is applied.

Referring now to the drawings, particularly to FIG. 1, an internal combustion engine 1 employed in the shown embodiment, is designed to be driven by a mixture fuel of a gasoline and an alcohol fuel, such as methanol. The engine 1 has an air induction system including an intake manifold 3. In the vicinity of an intake port of each combustion chamber, a fuel injection valve 2 is provided for injecting controlled amount of mixture fuel at controlled timings. Air/fuel mixture is formed in the air induction system and then introduced into the combustion chamber for combustioning therein. An air cleaner 4 and an air flow meter 5 are disposed in the air induction system in per se well known manner. As is well known, the air flow meter 5 monitors an intake air flow rate to provide an engine load indicative data Q. The engine 1 also has an exhaust passage 6 in which is disposed an oxygen sensor (not shown) to monitor oxygen concentration in an exhaust gas and whereby detects rich and lean of air/fuel mixture combustioned in the combustion chamber.

The fuel injection valve 2 is connected to a fuel tank 7 in which is stored the mixture fuel 8. A fuel pump 9 is disposed within the fuel tank 7 for sucking the mixture fuel 8 therein. The fuel pump 9 feeds the mixture fuel 8 through fuel feed line 10. A fuel filter 11 is disposed in the fuel feed line for filtering out foreign matters. A return line 13 with a pressure regulator 12 is connected to the fuel feed line 10 for returning the excess amount of fuel to the fuel tank 7.

Figure 2:
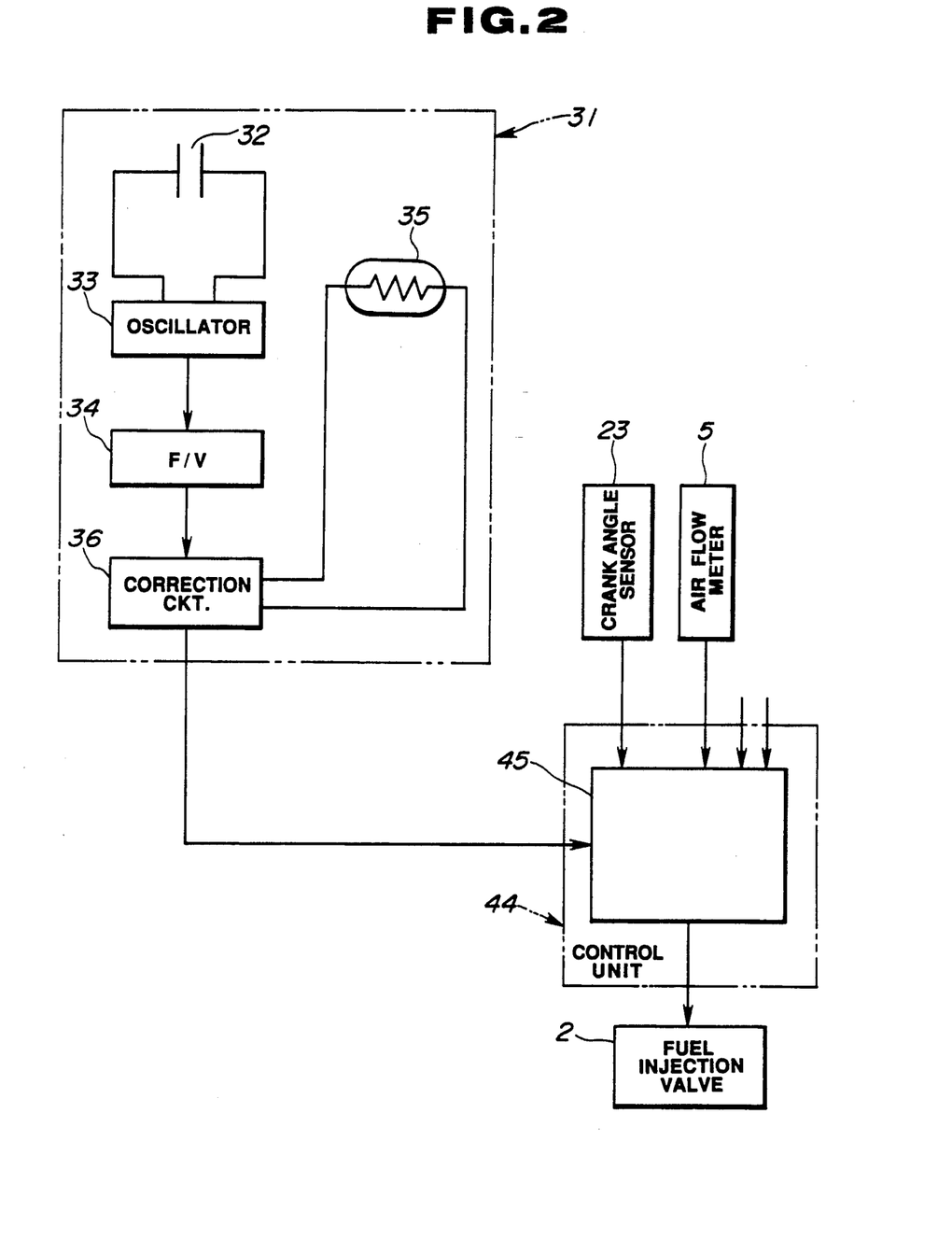
FIG. 2 is a block diagram of the preferred embodiment of the fuel concentration monitoring unit as combined with a control unit of the fuel injection control system.

The preferred embodiment of a fuel concentration monitoring unit 31 is provided in the fuel feed line 10 for monitoring alcohol concentration in the mixture fuel fed therethrough. The fuel concentration monitoring unit 31 includes an electrostatic capacity type sensor 32 which has a pair of electrodes. The sensor 32 monitors alcohol concentration in the mixture fuel by monitoring electrostatic capacity $C_s$ which is expressed by the foregoing equation. As shown in FIG. 2, the circuit of the preferred embodiment of the fuel concentration monitoring unit 31 includes an LC oscillation circuit 33 which produced a frequency signal variable of frequency f depending upon the electrostatic capacity $C_s$ monitored by the sensor 32. In practice, the frequency f of the frequency signal can be expressed by:

$$f = \tfrac{1}{2} \cdot \pi \cdot \sqrt{L(C_s + C_o)} \qquad (1)$$

wherein
L: inductance
$C_o$: capacity of circuit

The frequency signal of the LC oscillation circuit 33 is fed to a frequency-to-voltage (F/V) converter 34. The output voltage signal V of the F/V converter 34 is fed to a fuel temperature dependent error correction circuit 36. The correction circuit 36 is connected to a posistor 35 which monitors a temperature condition of the mixture fuel flowing through the fuel feed line 10.

Figure 3:
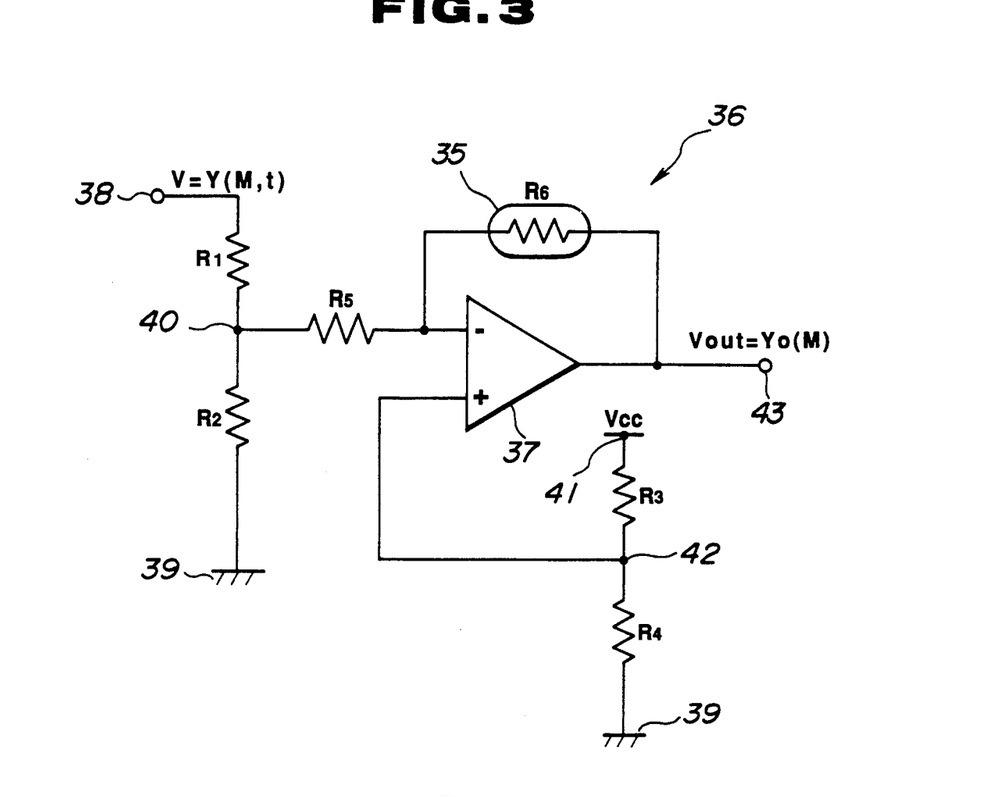
FIG. 3 is a circuit diagram of a fuel temperature dependent error correction circuit employed in the preferred embodiment of the fuel concentration monitoring unit.

As shown in FIG. 3, the correction circuit 36 includes an operational amplifier 37 which serves as an inverting amplifier. An input terminal 38 of the correction circuit 36 is connected to the F/V converter 34 to receive therefrom the output voltage signal V. The input terminal 38 is connected to the ground 39 via a voltage dividing resistors dividing resistors $R_1$ and $R_2$. A junction 40 between the dividing resistors $R_1$ and $R_2$ is connected to an inverting input of the operational amplifier 37 via a resistor $R_5$. The non-inverting input of the operational amplifier 37 is connected to a voltage divider constituted of voltage dividing resistors $R_3$ and $R_4$. The voltage dividing resistors $R_3$ and $R_4$ are connect a regulated power source 41 to receive therefrom a regulated power Vcc as a reference voltage to the ground 39. A junction 42 between the dividing resistors $R_3$ and $R_4$ is connected to the non-inverting input of the operational amplifier. The posistor 35 is connected between the output terminal 43 and the inverting input of the operational amplifier 37. As can be seen from FIG. 4, the posistor 35 has an output characteristics to increase resistance $R_6(\Omega)$ according to increasing of the fuel temperature t (°C.).

The fuel concentration monitoring unit 31 is connected to a control unit 44 which comprises a microprocessor. The control unit 44 is also connected to various sensors, such as the air flow meter, a crank angle sensor, an engine coolant temperature sensor, and so forth. The control unit 44 processes preselected parameter data for deriving fuel injection amount in a known manner. Namely, as is well known, the fuel injection amount is derived from the following equation:

$$Ti = Mk \cdot Tp \cdot \alpha \cdot \alpha' \cdot Coef + Ts \qquad (2)$$

where Tp: basic fuel injection amount expressed by $k \cdot Q/N$; (Q: engine load, N: engine speed)
  α: air/fuel ratio dependent feedback correction coefficient;
  α': basic air/fuel ratio learning correction coefficient
  Coef: various correction coefficient, such as acceleration enrichment correction coefficient, cold engine correction coefficient and so forth;
  Ts: battery voltage compensation value
  Mk: alcohol concentration dependent correction coefficient The control unit 44 feeds the fuel injection control pulse having a pulse width corresponding to the fuel injection amount Ti thus derived, to the fuel injection valve.

In the shown construction, as explanatorily illustrated in FIG. 2, the control unit 44 may formulate all by fuel injection control stage without incorporating a fuel temperature dependent error correction stage.

Through various experiments, it has been found that fuel temperature t may not influence for result monitoring of alcohol concentration at approximately 8% of alcohol concentration in the mixture fuel. When alcohol concentration in the mixture fuel is approximately 8%, the output voltage of the alcohol sensor 35 is maintained constant irrespective of the fuel temperature. Therefore, this alcohol concentration can be take as reference value.

Figure 5:
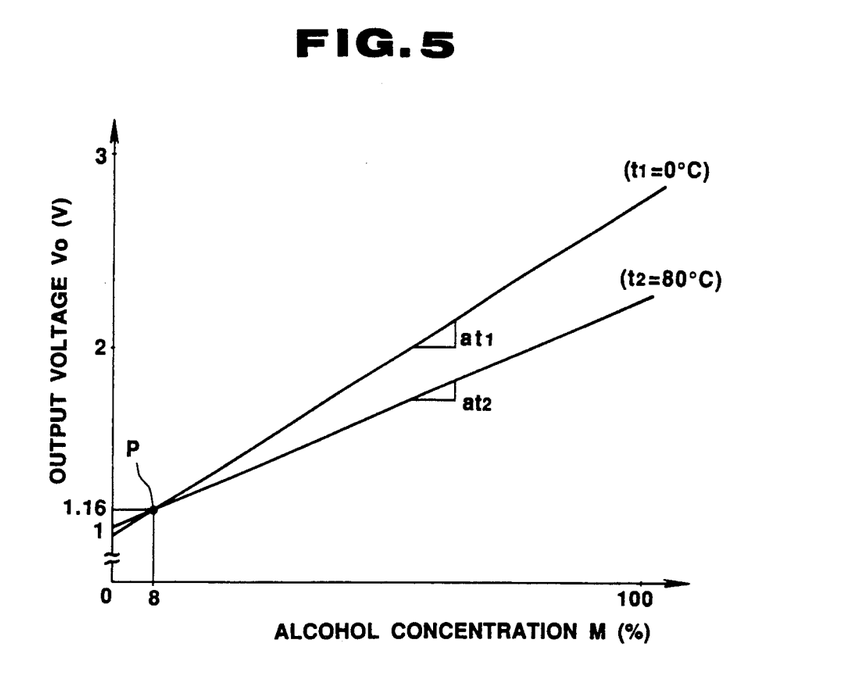
FIG. 5 is a chart showing relationship between an alcohol concentration and output voltage for obtaining a gradient of variation of output voltage depending upon alcohol concentration.
Figure 6:
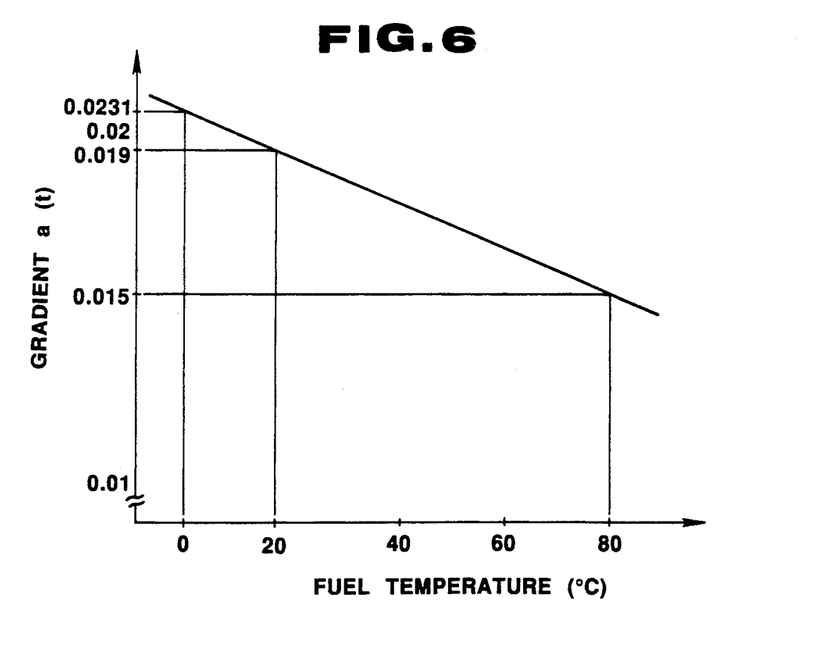
FIG. 6 is a chart showing relationship between fuel temperature and output voltage variation gradient.

Also, it was found that the gradient of variation of the output voltage at high fuel temperature is smaller than that at low fuel temperature, as shown in FIG. 5. In the example of FIG. 5, respective lines show variation of the output voltage at 80° C. and at 0° C. of fuel temperature. As can be clear from FIG. 5, the gradient at$_1$ at 0° C. is greater than the gradient at$_2$ at 80° C. Through experiments, variation of the gradient a(t) relative to the fuel temperature t can be illustrated as shown in FIG. 6. With tasking the variation characteristics of FIG. 6 as the gradient variation characteristics a(t), it can be expressed by:

$$a(t) = 0.0213 - 0.000066 \cdot t$$

$$\text{coefficient of corelation } \gamma = -0.999 \qquad (3)$$

From the result set forth above, the output voltage V of the F/V converter can be generally expressed by:

$$Y(M,t) = a(t) \cdot X(M) + b \quad (4)$$

where
Y(M,t)=V
X(M): alcohol concentration
b: output voltage at the reference value (8%)

On the other hand, with setting the fuel temperature 20° C. as reference temperature, and assuming that the gradient at the reference temperature is a₀ and the reference standard voltage at the reference temperature is Y₀(M), Y₀(M) can be expressed by:

$$Y_0(M) = a_0 \cdot X(M) + b \quad (5)$$

The foregoing equation (4) can be converted into:

$$X(M) = \{Y(M,t) - b\}/a(t) \quad (6)$$

Substituting X(M) in the foregoing equation with the equation (6), the foregoing equation (5) can be expressed as:

$$Y_0(M) = a_0 \cdot \frac{Y(M,t) - b}{a(t)} + b \quad (7)$$

Form FIG. 6, the gradient a₀ at the reference temperature (t=20° C.) is derived at 0.019. On the other hand, when the alcohol concentration is the reference value P (i.e. 8%), the output voltage b of the F/V converter 34 is 1.16. By substituting the elements in the foregoing equation (7) with the values set forth above and with the equation (3), the following equation can be established:

$$Y_0(M) = 0.019 \cdot \frac{Y(M,t) - 1.16}{0.0213 - 0.000066t} + 1.16 \quad (8)$$

Therefore, with utilizing the fuel temperature indicative output t of the posistor 35 and applying the output voltage V (=Y(M,t)) to the input terminal 38 of the fuel temperature dependent error correction circuit 36, an output voltage V_out at the reference temperature can be derived.

In the practical application of the logic of fuel temperature dependent error correction as set forth above, the output voltage V_out at the output terminal 43 of the fuel temperature dependent error correction circuit 36 can be expressed by:

$$V_{out} = \frac{R_6}{R_5}\left\{ \frac{R_4}{R_3 + R_4} \cdot Vcc - \frac{R_2}{R_1 + R_2} \cdot Y(M,t) \right\} + \frac{R_4}{R_3 + R_4} \cdot Vcc \quad (9)$$

Figure 4:
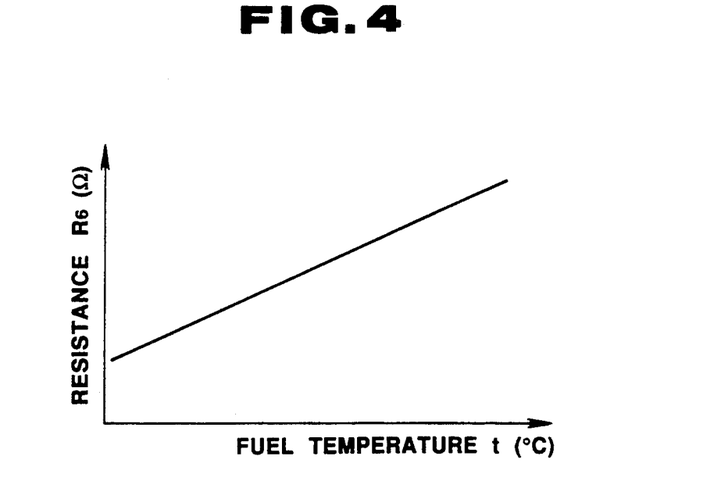
FIG. 4 is a chart showing characteristics of posistor employed in the fuel temperature dependent error correction circuit.

Here, the resistance R₆ of the posistor 35 varies in the characteristics as illustrated in FIG. 4. Therefore, assuming that the resistance of the posistor 35 at the reference temperature, i.e. 20° C. is R_{6.0}, the resistance R₆ can be expressed by:

$$R_6 = R_{6.0} \cdot (1 + \alpha t) \quad (10)$$

Since α can be generally expressed by:

$$\alpha \approx 3300 PPM/°K \leq 1 \quad (11)$$

R₆ can be expressed by:

$$R_6 \approx \frac{R_{6.0}}{1 - \alpha t} \quad (12)$$

Therefore, by substituting R₆ in the foregoing equation (9) with the equation (12), the following equation can be established.

$$V_{out} = \frac{-\left( \frac{R_2}{R_1 + R_2} \cdot Y(M,t) - \frac{R_4}{R_3 + R_4} \cdot Vcc \right)}{\frac{R_5}{R_{6.0}} \cdot (1 - \alpha t)} + \frac{R_4}{R_3 + R_4} \cdot Vcc \quad (13)$$

Here, assuming that $$\frac{R_4}{R_3 + R_4} \cdot Vcc = \text{constant} (\approx 1.16) \quad (14)$$

and adjusting the resistances of the resistors R₂ and R₅, substantially equivalent equation to that of equation (8) can be obtained.

It should be appreciated that, in the equation (13), the negative sign was necessitated for action of the fuel temperature dependent error correction circuit 36 as the inverting amplifier.

As set forth above, since the shown embodiment of the fuel concentration monitoring unit 31 incorporates the posistor 35 as the fuel temperature sensor, and the fuel temperature dependent error correction circuit 36 within the unit, fuel temperature compensation can be done together with inverting amplification. Therefore, the reference standard output voltage Y_O(M) at the fuel temperature 20° C. can be generated and fed to the control unit 44. Furthermore, with utilizing the reference value at the fuel temperature approximately 8° C., linear correction with the fuel temperature dependent correction value can be performed with the effect of the feedback of the posistor 35.

Therefore, the shown embodiment of the fuel concentration monitoring unit 31 according to the present invention is operable independently of the control unit 44. Therefore, inspection of this fuel concentration monitoring unit can solely be done. This makes inspection in production line easier. Furthermore, since the shown embodiment does not require to connect the fuel temperature sensor to the control unit independently of the fuel concentration monitoring unit, number of harness required can be reduced.

Figure 7:
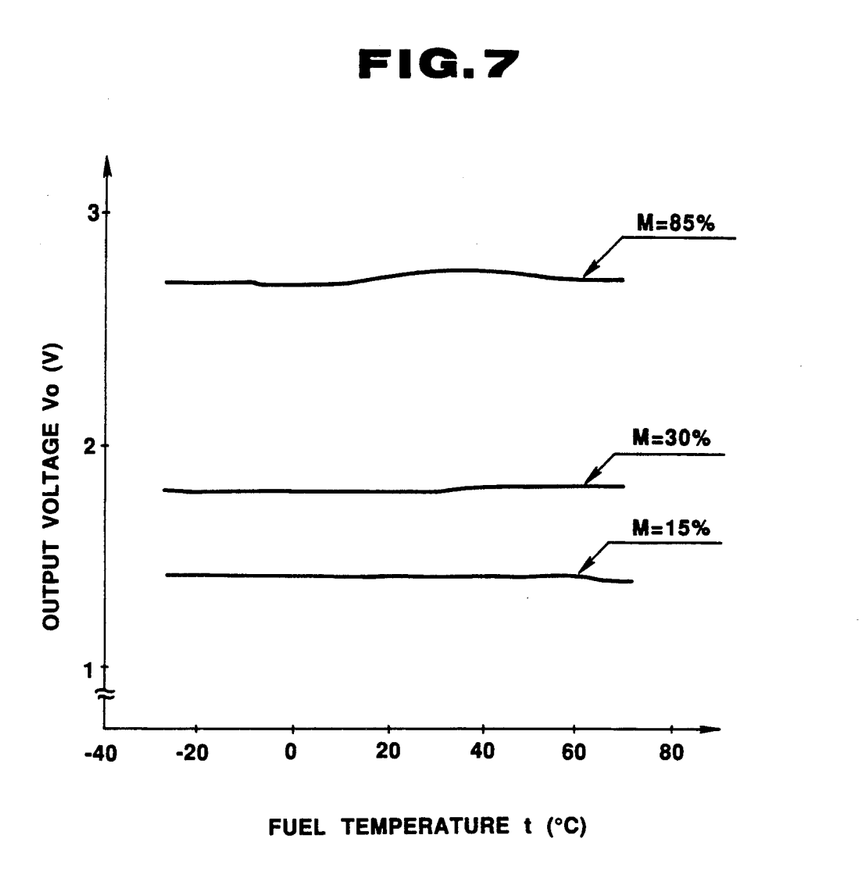
FIG. 7 is a chart showing result of fuel temperature dependent error correction performed in the preferred embodiment of the fuel concentration monitoring unit.

For demonstrating the performance of the shown embodiment of the fuel concentration monitoring unit 31, result of fuel temperature compensation for the alcohol concentrations M of 15%, 30% and 85% in the temperature range of −30° C. to 70° C. are illustrated in FIG. 7. As can be seen from FIG. 7, the shown embodiment shows substantially constant output voltage V₀ overall temperature range.

Figure 8:
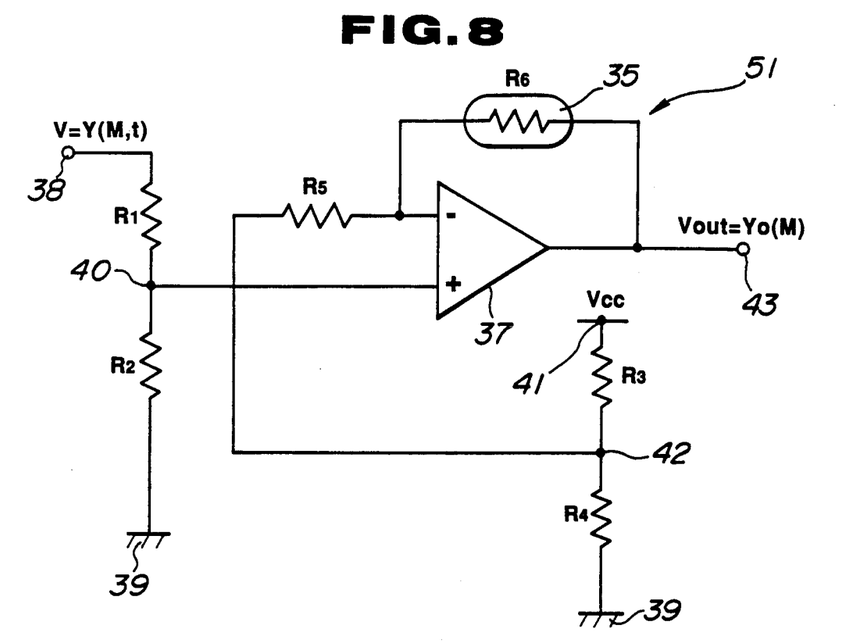
FIGS. 8 and 9 are circuit diagram of the second and third embodiment of the fuel temperature dependent error correction circuit to be employed in the preferred embodiment of the fuel concentration monitoring unit according to the invention.
Figure 9:
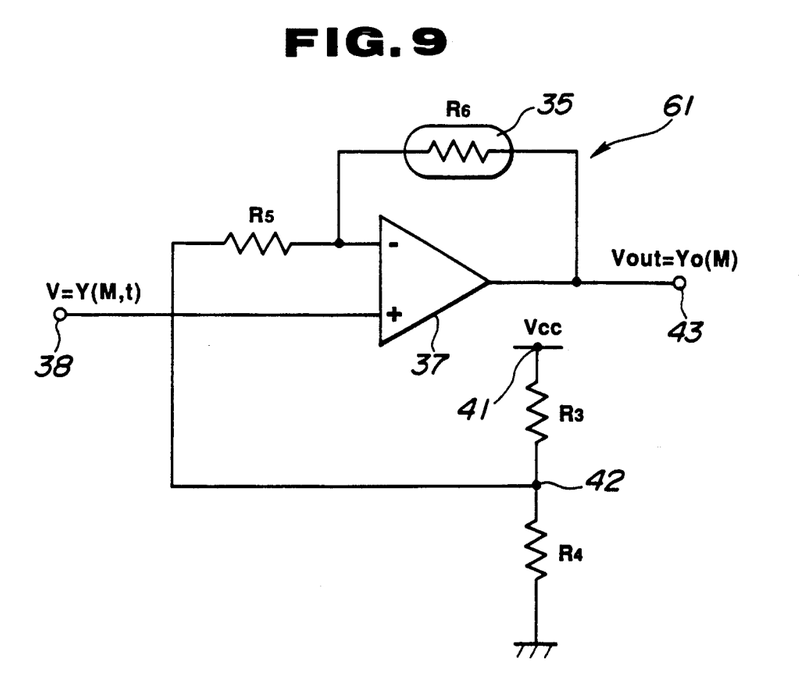

FIGS. 8 and 9 show modifications of the fuel temperature dependent error correction circuit 31. In the following discussion, the components common to the former embodiment will be represented by the same reference numerals. The shown modifications are featured by operation of the circuit as non-inverting amplifier.

Therefore, in these embodiments, the output voltage V of the F/V converter 34 is directly subject fuel temperature compensation.

In the embodiment of FIG. 8, the non-inverting input of the operational amplifier 37 in a fuel temperature dependent error correcting circuit 51 is connected to the junction 40 between the voltage dividing resistors $R_1$ and $R_2$. On the other hand, the junction 42 between the voltage dividing resistors $R_3$ and $R_4$ is connected to inverting input of the operational amplifier 37. With the shown construction, the output voltage $V_{out}$ output from the output terminal 43 of the fuel temperature dependent error correction circuit 51, at a reference temperature, can be expressed by:

$$V_{out} = \left(1 + \frac{R_6}{R_5}\right) \cdot \frac{R_2}{R_1 + R_2} \cdot Y(M,t) - \frac{R_6}{R_5} \cdot \frac{R_4}{R_3 + R_4} \cdot Vcc \qquad (15)$$
$$= \frac{R_6}{R_5} \cdot \left(\frac{R_2}{R_1 + R_2} \cdot Y(M,t) - \frac{R_4}{R_3 + R_4} \cdot Vcc\right) + \frac{R_2}{R_1 + R_2} \cdot Y(M,t)$$

Here, setting that $$\frac{R_4}{R_3 + R_4} \cdot Vcc = \text{constant} \ (\approx 1.16) \qquad (16)$$

and adjusting the resistances of the resistors $R_2$ and $R_5$, the reference standard voltage at 20° C. with satisfactory fuel temperature compensation can be obtained as non-inverted signal.

FIG. 9 shows the fuel temperature dependent error correction circuit 61 in further simplified form. Simplification of the circuit was made by neglecting the voltage dividing resistors $R_1$ and $R_2$. Because of absence of the resistors $R_1$ and $R_2$, the equation (15) in the former embodiment can be simplified as:

$$V_{out} = \left(1 + \frac{R_6}{R_5}\right) \cdot Y(M,t) - \frac{R_6}{R_5} \cdot \frac{R_4}{R_3 + R_4} \cdot Vcc \qquad (17)$$
$$= \frac{R_6}{R_5} \cdot \left(Y(M,t) - \frac{R_4}{R^3 + R^4} \cdot Vcc\right) - Y(M,t)$$

Therefore, substantially equivalent performance of fuel temperature compensation can be performed.

It should be appreciated, that though the shown second and third embodiments of the fuel temperature dependent error correction circuits 51 and 61 are formulated as non-inverting amplifier, it is, of course, possible to incorporate an inverting amplifier as that in the prior art to obtain inverted output of the F/V converter.

While the present invention has been discussed in terms of the preferred embodiments of the invention, the invention can be implemented in various ways. Therefore, the invention should be understood to include all possible embodiments and modifications which can be embodies without departing from the principle of the invention which is set out in the appended claims.

For example, though the shown embodiments employ posistor for monitoring the fuel temperature, any type of temperature sensors which enables the fuel temperature dependent correction for the fuel concentration indicative signal, are applicable. For instance, thermister can be used in place of the posistor. Furthermore, in the shown embodiment, the fuel concentration at 8% is taken as reference value, it may be possible to use the fuel concentration indicative signal value at 0% or 5% of the fuel concentration. Namely, the preferred range of fuel (alcohol) concentration to be used is 0 to 12% in practical use. However, setting the reference value at 8% of alcohol concentration may provide the most favorable result in temperature dependent error compensation.

What is claimed is:

1. An electrostatic capacity type fuel concentration monitoring unit comprising:
   a first sensor disposed within a mixture fuel containing a specific type of fuel in a variable mixture rate, said first sensor producing a first sensor signal indicative of concentration of said specific type of fuel;
   a second sensor disposed within said mixture fuel for monitoring temperature thereof, said second sensor generating a second sensor signal indicative of temperature of said mixture fuel;
   a circuit incorporated in said unit for generating a fuel concentration indicative signal which varies in a given rate across a predetermined reference value set at a predetermined fuel concentration, said circuit being responsive to said second sensor signal to correct said fuel concentration indicative signal value by varying said given rate depending upon said second sensor signal value.

2. An electrostatic capacity type fuel concentration monitoring unit as set forth in claim 1, wherein said circuit includes a frequency generator for generating a frequency signal variable of frequency depending upon fuel concentration of said specific type fuel in said mixture fuel, a frequency-to-voltage converter responsive to said frequency signal to produce a voltage signal as said fuel concentration indicative signal.

3. An electrostatic capacity type fuel concentration monitoring unit as set forth in claim 2, wherein said reference value is set at a fuel concentration, at which said fuel concentration indicative signal value contain minimum error depending upon fuel temperature represented by said second sensor signal.

4. An electrostatic capacity type fuel concentration monitoring unit as set forth in claim 3, wherein said circuit further includes an operational amplifier which receives said fuel concentration indicative signal at a first input terminal and a reference signal representative of said reference value at a second input terminal, and said second sensor is connected in a feedback circuit connecting an output terminal of said operational amplifier and said second input terminal.

5. An electrostatic capacity type fuel concentration monitoring unit as set forth in claim 1, which monitors an alcohol concentration in said mixture fuel which contains gasoline and alcohol in a variable rate.

6. A fuel injection control system for an automotive internal combustion engine which is designed to be driven by a mixture fuel of at least two mutually different type of fuels, comprising:
   a fuel injection valve disposed for injecting fuel into an induction system of said engine for forming an air/fuel mixture to be combustioned within a combustion chamber;

an engine operation monitoring means for monitoring preselected engine operating parameters to produce engine control parameter signal representative of an engine driving condition;

a fuel concentration monitoring unit for monitoring concentration of specific one of said fuels in said mixture fuel, said fuel concentration monitoring unit including a first sensor disposed within a mixture fuel containing a specific type of fuel in a variable mixture rate, said first sensor producing a first sensor signal indicative of concentration of said specific type of fuel;

a second sensor disposed within said mixture fuel for monitoring temperature thereof, said second sensor generating a second sensor signal indicative of temperature of said mixture fuel;

a circuit incorporated in said unit for generating a fuel concentration indicative signal which varies in a given rate across a predetermined reference value set at a predetermined fuel concentration, said circuit being responsive to said second sensor signal to correct said fuel concentration indicative signal value by varying said given rate depending upon said second sensor signal value; and a control unit receiving said engine control parameter signal for deriving a fuel injection amount on the basis thereof and correcting the fuel injection amount with a correction factor derived on the basis of the corrected fuel concentration indicative signal.

7. A fuel injection control system as set forth in claim 6, wherein said circuit includes a frequency generator for generating a frequency signal variable of frequency depending upon fuel concentration of said specific type fuel in said mixture fuel, a frequency-to-voltage converter responsive to said frequency signal to produce a voltage signal as said fuel concentration indicative signal.

8. A fuel injection control system as set forth in claim 7, wherein said reference value is set at a fuel concentration, at which said fuel concentration indicative signal value contain minimum error depending upon fuel temperature represented by said second sensor signal.

9. A fuel injection control system as set forth in claim 8, wherein said circuit further includes an operational amplifier which receives said fuel concentration indicative signal at a first input terminal and a reference signal representative of said reference value at a second input terminal, and said second sensor is connected in a feedback circuit connecting an output terminal of said operational amplifier and said second input terminal.

10. A fuel injection control system as set forth in claim 6, which monitors an alcohol concentration in said mixture fuel which contains gasoline and alcohol in a variable rate.

* * * * *